(12) United States Patent
Herder et al.

(10) Patent No.: US 6,447,532 B1
(45) Date of Patent: Sep. 10, 2002

(54) MANIPULATING PLIERS

(75) Inventors: Justus Laurens Herder, Rotterdam; Marcel Jeroen Horward, Arnhem, both of (NL)

(73) Assignee: Kunst & Van Leerdam Medical Technology B.V., Enschede (NL)

( * ) Notice: Subject to any disclaimer, the term of this patent is extended or adjusted under 35 U.S.C. 154(b) by 0 days.

(21) Appl. No.: 09/269,096

(22) PCT Filed: Sep. 15, 1997

(86) PCT No.: PCT/NL97/00521

§ 371 (c)(1),
(2), (4) Date: Jul. 7, 1999

(87) PCT Pub. No.: WO98/11833

PCT Pub. Date: Mar. 26, 1998

(30) Foreign Application Priority Data

Sep. 18, 1996 (NL) .............................................. 1004056

(51) Int. Cl.[7] .............................. A61B 7/28; B25B 7/02
(52) U.S. Cl. .......................... 606/208; 606/207; 81/415
(58) Field of Search .................... 606/1, 174, 205–210, 606/51, 52; 81/4, 5

(56) References Cited

U.S. PATENT DOCUMENTS

| | | | | |
|---|---|---|---|---|
| 1,754,806 A | * | 4/1930 | Stevenson | 606/174 |
| 4,267,608 A | | 5/1981 | Bora, Jr. | |
| 4,558,911 A | | 12/1985 | Ruoff | |
| 5,147,373 A | | 9/1992 | Ferzli | |
| 5,152,780 A | * | 10/1992 | Honkanen et al. | 606/205 |
| 5,176,699 A | | 1/1993 | Markham | |
| 5,201,743 A | | 4/1993 | Haber et al. | |
| 5,263,967 A | * | 11/1993 | Lyons, III et al. | 606/205 |
| 5,275,615 A | | 1/1994 | Rose | |
| 5,281,230 A | * | 1/1994 | Heidmueller | 606/208 |

* cited by examiner

Primary Examiner—John G. Weiss
Assistant Examiner—Michael Bogart
(74) Attorney, Agent, or Firm—Jeffrey D. Myers; Rod D. Baker

(57) ABSTRACT

The invention relates to manipulating pliers especially but not exclusively for surgical purposes, comprising a frame, at a first side of the frame a control handle and at a second side opposite the first side of the frame a gripper as well as a coupling between the control handle and the gripper. The control handle and the gripper are each coupled to the frame by means of a roller bearing.

16 Claims, 3 Drawing Sheets

MANIPULATING PLIERS

BACKGROUND OF THE INVENTION

1. Field of the Invention

The invention relates to manipulating pliers, especially but not exclusively for surgical purposes, comprising a frame, at a first end of the frame a control handle and at a second end opposite the first end of the frame a gripper as well as a coupling element between the control handle and the gripper.

2. Description of the Related Art

Manipulating pliers are used in particular for so-called laparoscopic surgery, wherein a few small incisions are made in the abdominal wall of a patient to allow the insertion of the manipulating pliers. Such minimally invasive surgery is patient-friendly and is increasingly preferred. The known manipulating pliers is available in two diameters, namely one in which the frame is formed by an elongated tube, having an outside diameter of 5 mm, and one embodiment in which said diameter is 10 mm. Through this frame of the known manipulating pliers runs a rod-like coupling between the control handle which, when the manipulating pliers are being used, is placed in a hand of the surgeon, and the gripping member which is inserted into the patient.

Surgical operations using the known manipulating pliers, encounter difficulties because of inadequate ability to feel with said manipulating pliers. Another disadvantage is that the precision of the known manipulating pliers as problematic due to play in the couple in between the control handle and the gripper. Another problem of the known manipulating pliers is that the gripper which comprises two interacting gripping members, requires a non-constant actuating force, depending on the opening angle between the interacting gripping members fact that the internal rigidity of the known manipulating pliers is low is also a problem: the coupling between the control handle and the gripper is slack, with the result that when a rigid object is gripped, it is not perceived as being rigid.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE INVENTION

Figure 1A:
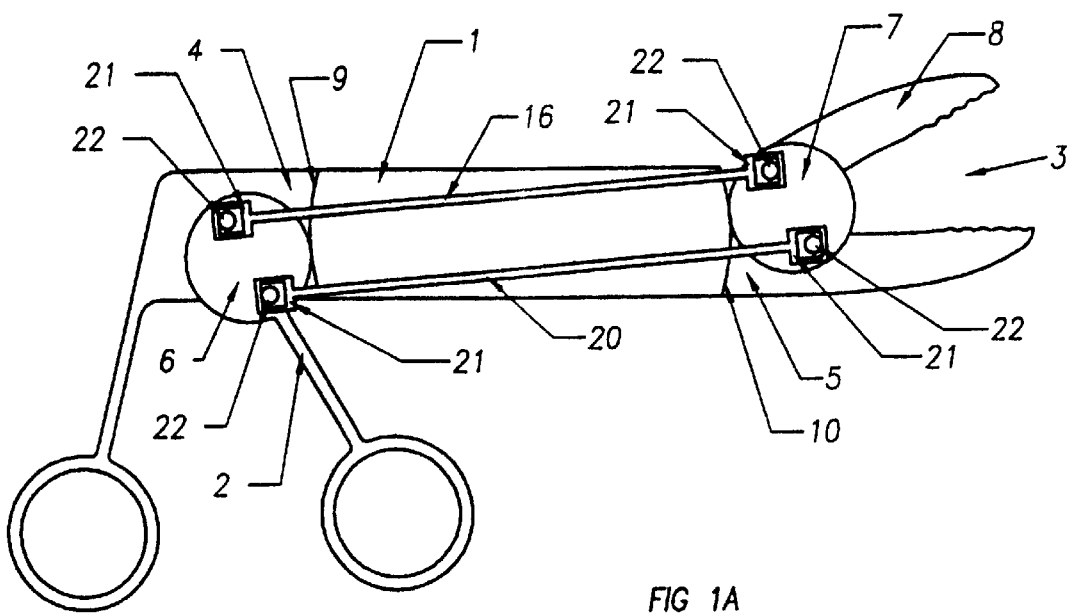
FIG. 1A is a side view of a preferred embodiment of the apparatus of the invention, shown in an open position.

It is the objective of the invention to solve the problems of known manipulating pliers and to provide further advantages which will be explained below.

The manipulating pliers according to the invention is characterized in that the gripper comprises at least one movable gripping member and that the control handle and the movable gripping member are each coupled to the frame by a rolling bearing arranged between the frame and the control handle and the movable gripping member respectively. As a result it becomes unimportant that because of the surgical nature of the application the lubrication must be absent, and thus manipulating pliers are provided in which the frictional component in the force necessary to operate the manipulating pliers, is greatly reduced. The manipulating pliers according to the invention have been shown to require less than 4% of the applied actuating force to overcome the friction. The performance-efficiency of the manipulating pliers according to the invention is thus more than 96%. In contrast, the mechanical efficiency of the known manipulating pliers is not more than 30%.

An advantageous embodiment of the manipulating pliers according to the invention is characterized in that the control handle comprises a lever, which at the end of the frame is provided with a cylindrical contact surface engaging a first contact surface provided on the frame, and that the movable gripping member is provided with a cylindrical contact surface at the end of the frame engaging a second contact surface provided on the frame. The rolling bearing is thus formed by the cylindrical contact surfaces at the control handle and the gripper, engaging the first and second frame contact surface of the frame.

By providing the manipulating pliers with a circular first and second frame contact surface formed as circular segments having identical radii, the movement undergone by the control handle can be transmitted to the movable gripping member at a one-to-one ratio. It is then desirable that the first and second frame contact surface are positioned on the frame such that their centres of curvature are identical, to ensure that the length of the coupling between the control handle and the gripper is not variable.

Preferably each rolling bearing being formed by the first, respectively the second frame contact surface for the one part and the cylindrical contact surface of the control handle respectively the movable gripping member for the other part, is provided with a first and a second flexible strap each of which is connected by an end with the first, respectively the second frame contact surface, is led between this first respectively second frame contact surface and the cylindrical contact surface of the control handle or from the movable gripping member engaging therewith, and which is connected with the other end to the cylindrical contact surface of the control handle, respectively the movable gripping member, and on which is provided a third flexible strap displaced in the extended direction of the first and second flexible straps, which is likewise connected between and near the connection of the first and second flexible strap, with the cylindrical contact surface of the control handle, respectively the movable gripping member, and from there is led through, as extension of the first and second flexible strap between the first, respectively the second frame contact surface and the therewith engaging cylindrical contact surface of the control handle, respectively the movable gripping member, to be likewise connected at a position removed from the connection of the first and second flexible straps to the first, respectively the second frame contact surface. In this manner the occurrence of slip in the rolling bearings is prevented and the manipulating pliers' sturdiness is increased, so that they are able to absorb the tangential forces developing with regard to the engaging contact surfaces, without disturbing the rolling engagement of said contact surfaces.

In a practical embodiment, the first, the second and the third flexible strap are interconnected by means of a cross piece. The number of flexible straps can easily be increased.

When operating the manipulating pliers, the engaging contact surfaces can roll over each other while the flexible straps, which may run alongside each other, bend to accommodate the motion. The best results have been obtained if each flexible strap has a thickness chosen in proportion to the smallest radius of the rolling bearing.

A practical embodiment of the manipulating pliers according to the invention which can be realized relatively simply, is characterized in that the control handle is provided with a control roller comprising the contact surface engaging the first frame contact surface, and the movable gripping member is provided with a gripping member roller comprising the contact surface engaging the second frame contact surface, and that the control roller and the gripping member roller are coupled to each other to be substantially torque-resistant. This provides very direct coupling between the movement of the gripping member and the control member, so that there is optimal feed-back of the forces exerted on the gripping member to the control handle.

A variety of embodiments is possible for the realization of the torque-resistant coupling between the gripping member roller and the control handle roller. To this end the coupling of the controlling roller and the gripping member roller preferably comprises at least a tension rod. In addition to the tension rod one or more spring elements may be provided. The advantage of such a solution employing spring elements is that, due to the spring action, the different components of the manipulating pliers require no individual adjustment.

In a first preferred embodiment two spring elements may be provided, wherein a first spring element couples the control roller to the frame, and the second spring element couples the gripping member roller to the frame, and wherein said two spring elements are in balance with each other. Balanced spring elements signifies that when the first spring element is put under tension, the second spring element is released, such that the tensioning energy required to put the one spring under tension becomes available when the tension of the other spring is released, so that it seems as if there are no springs.

A second embodiment of the manipulating pliers with spring elements is characterized in that there is only one spring element coupling the control roller to the gripping member roller. This prevents incomplete balancing of the springs, if there are two, adversely affecting the working of the manipulating pliers.

In a third embodiment the manipulating pliers are according to the invention characterized in that the coupling of the control roller and the gripping member roller comprises two tension rods. This provides a completely rigid connection between the control roller and the gripping member roller, but requires some adjustment for tensioning the two tension rods. This can be done quite simply by designing the manipulating pliers such that the frame is in two parts, such that the distance between the first frame contact surface and the second frame contact surface is adjustable.

In order to realize all advantages of the invention it is desirable that the coupling of each tension rod with the control roller and the gripping member roller is provided with a rolling bearing.

In an advantageous embodiment the tension rod is provided at each end with an eye to receive a cylindrical pin which is coupled with the control roller respectively the gripping member roller. According to the invention the side of the eye in contact with the pin should have the shape of a circle segment whose radius is equal to half the distance between the sides of the eyes provided at both sides of the tension rod being in contact with the pins.

Figure 1B:
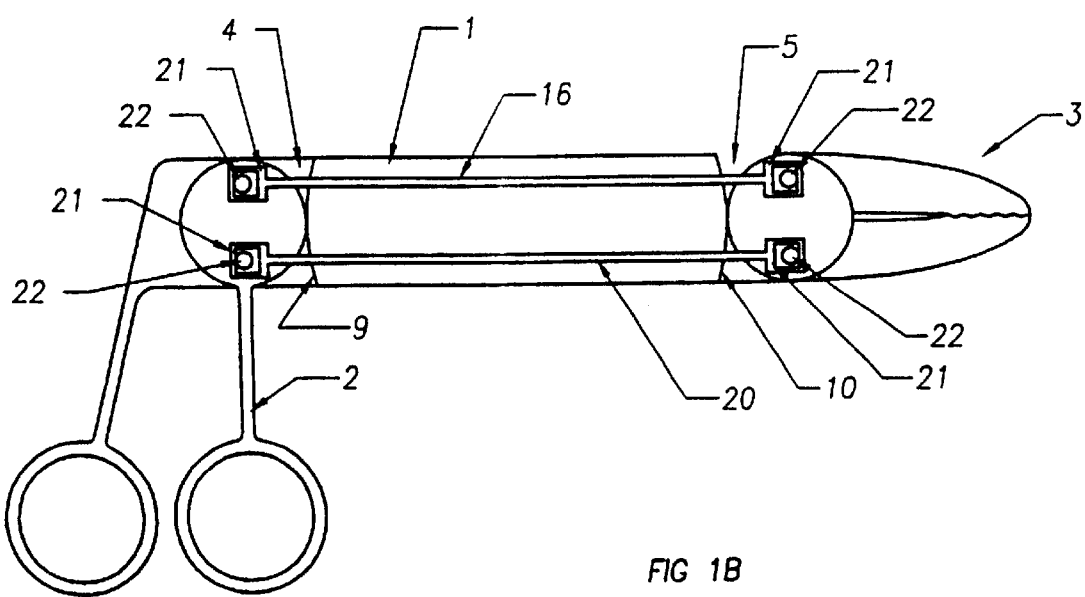
FIG. 1B is a side view of the embodiment of the invention depicted in FIG. 1A, shown in a closed position.
Figure 2:
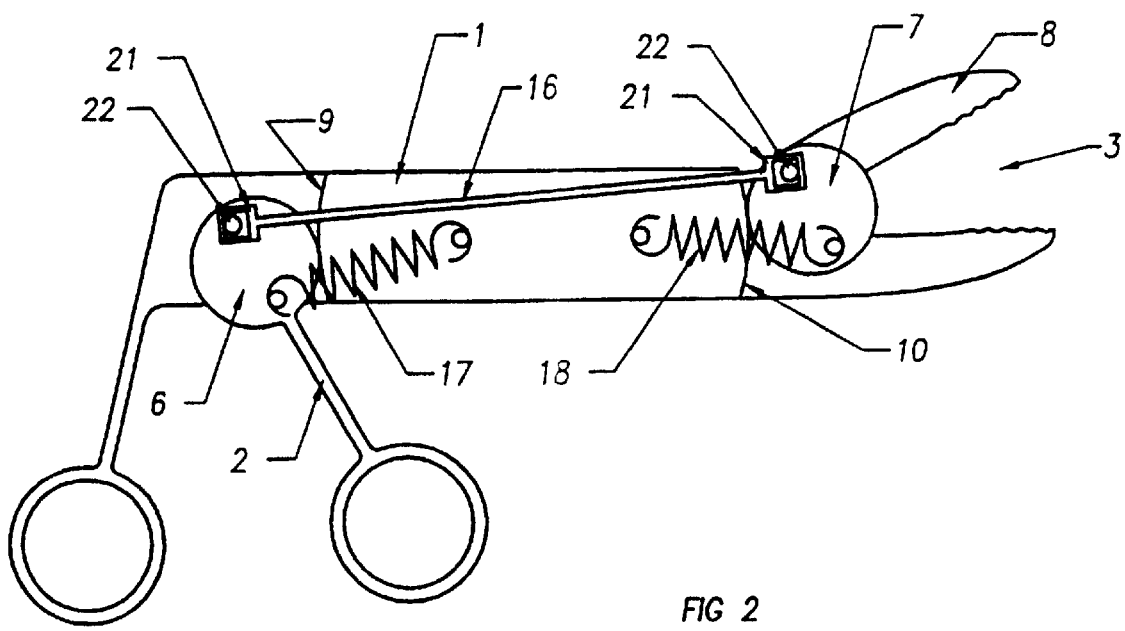
FIG. 2 is a side view of an alternative embodiment of the apparatus of the invention, showing the inclusion of a pair of springs as coupling elements.
Figure 3:
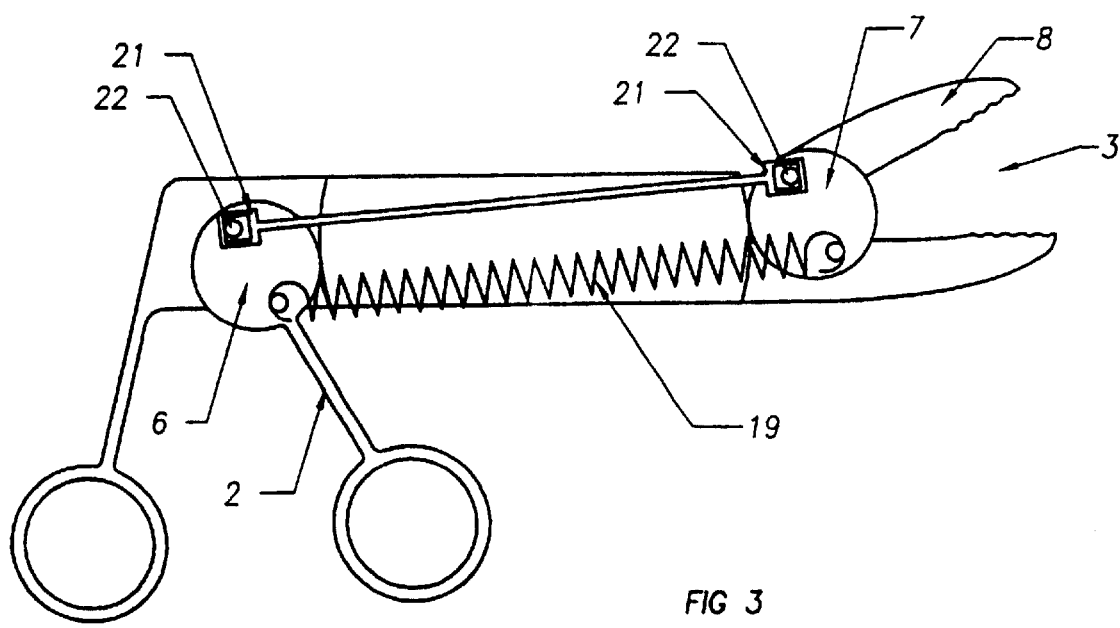
FIG. 3 is a side view of another alternative embodiment of the apparatus of the invention, showing the inclusion of a spring and a tension rod as coupling elements.
Figure 4:
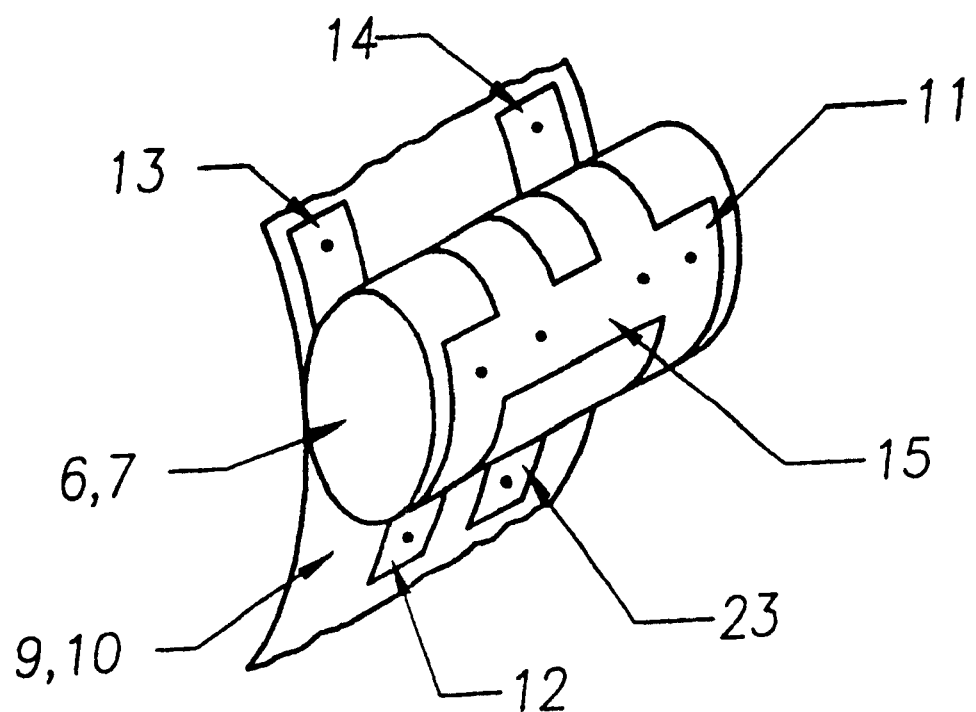
FIG. 4 is a perspective side view, slightly enlarged, of a portion of the apparatus according to the invention, showing the plurality of flexible straps that ameliorate slippage between the roller bearing surfaces of the apparatus.

The invention will now be further elucidated with reference to the drawing, in which:

FIGS. 1a and 1b show the manipulating pliers according to the invention in a first embodiment;

FIG. 2 shows the invention in a second embodiment;

FIG. 3 shows the manipulating pliers according to the invention in a third embodiment; and FIG. 4 shows a component of a rolling bearing of the manipulating pliers according to the invention.

Identical reference numbers used in the drawing refer to identical components.

The FIGS. 1a, 1b, 2 and 3 show manipulating pliers comprising a frame 1, a control handle 2 and a gripper 3. Both the control handle 2 and the gripper 3 are provided with a rolling bearing 4, 5. This rolling bearing 4, 5 comprises a roller 6, respectively 7, which is part of the control handle 2, respectively a movable gripping member 8. The rollers 6 and 7 have a cylindrical contact surface and said contact surfaces engage a first frame contact surface 9 and a second frame contact surface 10. The first frame contact surface 9 and the second contact surface 10 are formed like circle segments and have identical radii. Likewise, in the embodiments shown, the first and second frame contact surface 9, 10 are positioned on the frame 1 such that they have an identical centre of curvature, so that said frame contact surfaces 9, 10 form part of one and the same imaginary cylinder, as it were.

FIG. 4 shows in detail that the rollers 6, 7 and the first, respectively second frame contact surface 9, 10 are interconnected by means of a number of flexible straps 12, 13, 14, 23 each of which are connected both with the first, respectively the second frame contact surface 9, 10, and with the roller 6, respectively 7. Such flexible straps may be formed from a thin plate of stainless steel that may be unrolled without much resistance by displacing the roller 6, 7 over the first, respectively second frame surface 9, 10.

As is clearly shown in FIG. 4, a first flexible strap 13, and a second flexible strap 14 are connected at one end to the first, respectively the second frame contact surface 9, 10 and are led between the first, respectively second frame contact surface 9, 10 and the roller 6, 7 while being connected at their other end with the roller 6, 7. In addition there is always provided a third flexible strap 12 or 23 affixed in the extended direction of the first and second flexible straps 13, 14, which is likewise connected between and near the connection of the first and second flexible straps 13, 14 with the roller 6, 7 and from there is led, as extension of the first and second flexible straps 13, 14 between the first, respectively the second frame contact surface 9, 10 and the roller 6, 7 to be likewise connected to the first, respectively the second frame contact surface 9, 10 at a position removed from the connection of the first and second flexible straps 13, 14 to the first, respectively the second frame contact surface 9, 10. The Figure further shows clearly that use is made of two flexible straps indicated by reference numbers 13 and 14, and additionally, between and in the extended direction of said straps, of two flexible straps carrying reference numbers 12 and 13. This is done in order to allow the tension rods 16, 20 (to be further explained below), engaging the middle of the roller 6, 7, to be led through. A practical embodiment of one thing and another is shown clearly in FIG. 4, i.e. the application of a cross piece 15 by which all flexible straps 13, 14 and 12, 23 are interconnected.

The optimal thickness of the flexible straps 12, 13, 14, 23 may be chosen by taking into account the breaking strength respectively the rolling resistance of said straps. The optimal thickness of the flexible strap 11 depends on the smallest radius of the engaging contact surfaces of the rolling bearing; in this case the radius of the roller 6, 7. The thickness of the flexible strap is chosen in proportion with the above-mentioned smallest radius.

FIGS. 1a, 1b, 2 and 3 clearly show that the control handle 2 is provided with a control roller 6 bearing the contact surface engaging the first frame contact surface 9, and that the movable gripping member 8 is provided with a gripping member roller 7 bearing the contact surface engaging the second frame contact surface 10 and that control roller 6 and the gripping member roller 7 are connected substantially torque-resistantly. In all the embodiments shown, the coupling of the control roller 6 and the gripping member roller 7 comprises at least a tension rod 16. FIG. 2 shows that the coupling of the control roller 6 and the gripping member roller 7 further comprises spring elements 17 and 18 which balance each other out, wherein a first spring element 17 couples the control roller 6 to the frame 1 and the second spring element 18 couples the gripping member roller 7 to the frame 1. FIG. 3 shows another preferred embodiment, comprising only one spring element 19 which directly couples the control roller 6 to the gripping member roller 7. FIGS. 1a and 1b show yet another embodiment, i.e. one in which the coupling of the control roller 6 and the gripping member roller 7 comprises two tension rods 16 and 20.

Thanks to the use of spring elements 17, 18 and 19, the embodiments shown in FIGS. 2 and 3 do not require any adjustment for the tensioning of the tension rod 16. The use of the spring elements 17, 18 and 19 practically automatically provides a play-free coupling between the control roller 6 and the gripping member roller 7. This is not so in the embodiment shown in FIGS. 1a and 1b, wherein the tension rods 16 and 20 provide rigid coupling between the control roller 6 and the gripping member roller 7. To be able to adjust said tension rods 16 and 20, it is essential that the first contact surface 9 and the second frame contact surface 10 can be moved away from each other. To this end the frame 1 is executed as two parts (not shown) such that the distance between the first frame contact surface 9 and the second frame contact surface 10 is adjustable. This may be carried out in a manner generally known to an expert, so there is no need to go into further detail concerning the two-partness of the frame 1.

Both tension rods 16 and 20 are coupled with the control roller 6, respectively the gripping member roller 7 by means of a rolling bearing. To this end each tension rod 16, 20 is provided at each end with an eye 21 to receive a cylindrical pin 22 which is coupled with the control roller 6 respectively the gripping member roller 7. The side of each eye that is in contact with a pin 22, is formed as circle segment whose radius is equal to half the distance between the sides of the eyes 21 that are provided at both sides of the tension rod 16 respectively 20, which are in contact with the pins 22.

What is claimed is:

1. Manipulating pliers comprising a frame, a control handle at a first end of said frame, a gripper at a second end of said frame opposite the first end of said frame, and at least one coupling member extending between said control handle and said gripper, wherein said gripper comprises at least one movable gripping member, and further wherein said control handle and said movable gripping member are each coupled to said frame by a rolling bearing arranged between said frame and said control handle and said movable gripping member respectively.

2. Manipulating pliers according to claim 1 wherein said control handle comprises a lever, said lever comprising a cylindrical contact surface engaging a first frame contact surface on the first end of said frame.

3. Manipulating pliers according to claim 2 wherein said at least one movable gripping member comprises a cylindrical contact surface engaging a second frame contact surface on the second end of said frame.

4. Manipulating pliers according to claim 3 wherein said first and second frame contact surfaces define circle segments and have identical radii.

5. Manipulating pliers according to claim 4 wherein said first and second frame contact surfaces are positioned on said frame such that their centers of curvature are identical.

6. Manipulating pliers according to claim 1 wherein said rolling bearings comprise first and second frame contact surfaces and cylindrical contact surfaces on said control handle and on said movable gripping member, and said pliers additionally comprise a plurality of flexible straps to prevent slippage of said rolling bearings.

7. Manipulating pliers according to claim 6 wherein said plurality of flexible straps are interconnected by a cross piece.

8. Manipulating pliers according to claim 6 wherein each flexible strap has a thickness proportional to a smallest radius of the rolling bearings.

9. Manipulating pliers according to claim 3 wherein said control handle further comprises a control roller comprising said first cylindrical contact surface engaging said first frame contact surface, and said movable gripping member further comprises a gripping member roller comprising said second cylindrical contact surface engaging said second frame contact surface, and said control roller and said gripping member roller are coupled to each other by said at least one coupling element to be substantially torque-resistant.

10. Manipulating pliers according to claim 9 wherein said at least one coupling element comprises a tension rod.

11. Manipulating pliers according to claim 9 wherein said at least one coupling element comprises at least one spring element.

12. Manipulating pliers according to claim 11 wherein said at least one coupling element comprises two spring elements, wherein a first spring element couples said control roller to said frame, and said second spring element couples said gripping member roller to said frame, and wherein said spring elements are in balance with each other.

13. Manipulating pliers according to claim 9 wherein said at least one coupling element comprises two tension rods.

14. Manipulating pliers according to claim 13 wherein the ends of each tension rod are connected with said control roller and with said gripping member roller by a pin- and eye connection.

15. Manipulating pliers according to claim 14, characterized in that the tension rod (16, 20) is provided at each end with an eye (21) to receive a cylindrical pin (22) which is coupled with the control roller (6) respectively the gripping member roller (7).

16. Manipulating pliers according to claim 15 wherein a side of each eye in contact with a pin has a shape of a circle segment whose radius is equal to half the distance between the sides of each eye provided at each end of said tension rod.

* * * * *